(12) United States Patent
Kuck et al.

(10) Patent No.: US 11,395,616 B2
(45) Date of Patent: Jul. 26, 2022

(54) CATHETER ASSEMBLIES, OXYGEN-SENSING ASSEMBLIES, AND RELATED METHODS

(71) Applicants: SWSA Medical Ventures, LLC, Pleasant Grove, UT (US); University of Utah Research Foundation, Salt Lake City, UT (US)

(72) Inventors: Kai Kuck, Park City, UT (US); Natalie A. Silverton, Salt Lake City, UT (US); Spencer B. Shumway, South Jordan, UT (US); Bradley J. Stringer, Kaysville, UT (US)

(73) Assignees: WSA Medical Ventures, LLC, Pleasant Grove, UT (US); University of Utah Research Foundation, Salt Lake City, UT (US)

( * ) Notice: Subject to any disclaimer, the term of this patent is extended or adjusted under 35 U.S.C. 154(b) by 417 days.

(21) Appl. No.: 16/121,372

(22) Filed: Sep. 4, 2018

(65) Prior Publication Data
US 2019/0069831 A1    Mar. 7, 2019

Related U.S. Application Data

(60) Provisional application No. 62/555,161, filed on Sep. 7, 2017.

(51) Int. Cl.
*A61B 5/20* (2006.01)
*A61B 5/01* (2006.01)
(Continued)

(52) U.S. Cl.
CPC ............. *A61B 5/208* (2013.01); *A61B 5/01* (2013.01); *A61B 5/1459* (2013.01);
(Continued)

(58) Field of Classification Search
CPC ....... A61B 5/208; A61B 5/01; A61B 5/14507; A61B 5/1459; A61B 5/1473; A61B 5/201;
(Continued)

(56) References Cited

U.S. PATENT DOCUMENTS 5,389,217 A    2/1995  Singer
5,916,153 A *  6/1999  Rhea, Jr. ............... A61B 5/036
                                              600/310
(Continued)

FOREIGN PATENT DOCUMENTS

WO    2009/024985 A1    2/2009
WO    2014/043650 A2    3/2014
(Continued)

OTHER PUBLICATIONS

Written Opinion of the International Searching Authority for PCT Application No. PCT/US2018/049603, dated Jan. 11, 2019, 10 pages.
(Continued)

*Primary Examiner* — Patrick Fernandes
(74) *Attorney, Agent, or Firm* — TraskBritt

(57) ABSTRACT

An oxygen-sensing assembly for attachment to a urinary catheter may include a housing having a flow pathway extending between an inlet end and an outlet end thereof, an oxygen sensor in operable communication with the flow pathway of the housing, the oxygen sensor configured to detect oxygen levels of a fluid flowing through the flow pathway, a flowrate sensor configured to detect a flowrate of the fluid flowing through the flow pathway, and a temperature sensor configured to detect a temperature of the fluid flowing through the flow pathway.

26 Claims, 5 Drawing Sheets

(51) Int. Cl.
| | |
|---|---|
| A61B 5/00 | (2006.01) |
| A61B 5/1459 | (2006.01) |
| A61B 5/1473 | (2006.01) |
| A61B 5/145 | (2006.01) |
| A61B 5/1468 | (2006.01) |
| A61B 5/1455 | (2006.01) |

(52) U.S. Cl.
CPC ........ *A61B 5/1473* (2013.01); *A61B 5/14507* (2013.01); *A61B 5/201* (2013.01); *A61B 5/6852* (2013.01); *A61B 5/6853* (2013.01); *A61B 5/1455* (2013.01); *A61B 5/1468* (2013.01)

(58) Field of Classification Search
CPC ... A61B 5/6852; A61B 5/6853; A61B 5/1455; A61B 5/1468
See application file for complete search history.

(56) References Cited

U.S. PATENT DOCUMENTS

| | | | |
|---|---|---|---|
| 6,602,243 | B2 | 8/2003 | Noda |
| 7,060,038 | B2 | 6/2006 | Letort et al. |
| 8,827,924 | B2 | 9/2014 | Paz et al. |
| 9,662,058 | B2 | 5/2017 | Burnett et al. |
| 2002/0161314 | A1 | 10/2002 | Sarajarvi |
| 2004/0193021 | A1 | 9/2004 | Zdeblick et al. |
| 2006/0100743 | A1 | 5/2006 | Townsend et al. |
| 2008/0033425 | A1 | 2/2008 | Davis et al. |
| 2008/0249388 | A1* | 10/2008 | Kumhyr .............. A61B 5/00 600/368 |
| 2009/0043184 | A1 | 2/2009 | Fjield et al. |
| 2011/0201956 | A1 | 8/2011 | Alferness et al. |
| 2013/0237901 | A1* | 9/2013 | Woo .............. A61F 7/0085 604/24 |
| 2014/0378792 | A1* | 12/2014 | Krimsky .......... A61M 16/0484 600/310 |
| 2016/0183819 | A1 | 6/2016 | Burnett et al. |
| 2016/0310711 | A1* | 10/2016 | Luxon .............. A61M 1/0031 |
| 2017/0086746 | A1 | 3/2017 | Ofek et al. |
| 2017/0136209 | A1 | 5/2017 | Burnett et al. |
| 2017/0196478 | A1* | 7/2017 | Hunter .............. A61B 5/6847 |
| 2019/0150801 | A1 | 5/2019 | Suehara et al. |

FOREIGN PATENT DOCUMENTS

| | | |
|---|---|---|
| WO | 2015/105916 A1 | 7/2015 |
| WO | 2017/168541 A1 | 10/2016 |
| WO | 2017/213237 A1 | 12/2017 |
| WO | 2018/083487 A1 | 5/2018 |

OTHER PUBLICATIONS

International Search Report for PCT Application No. PCT/US2018/049603, dated Jan. 11, 2019, 3 pages.
Kainuma et al: "Continuous urine oxygen tension monitoring in patients undergoing cardiac surgery", Journal of Cardiothoracic and Vascular Anesthesia, Elsevier, Amsterdam, NL, vol. 10, No. 5, Aug. 1, 1996 (Aug. 1, 1996), pp. 603-608.
Supplementary European Search Report and Search Opinion Received for EP Application No. 18853477, dated on Feb. 15, 2021, 11 pages.
Tsukada Kosuke et al: "Development of catheter-type optical oxygen sensor and applications to bioinstrumentation", Biosensors and Bioelectronics, vol. 18, No. 12, Oct. 1, 2003 (Oct. 1, 2003), pp. 1439-1445.
Thakar et al., "A Clinical Score to Predict Acute Renal Failure After Cardiac Surgery," J. Am. Soc. Nephrol, vol. 16, (2005), pp. 162-8.
Tolley et al., "Effect of i.v. Furosemide on Pelvic Urinary Oxygen Tension in Humans," British Journal of Anaesthesia, vol. 83, No. 2, (1999), pp. 328-329.
Wang et al., "Optical methods of sensing and imaging oxygen: materials, spectroscopies and applications," Chem. Soc. Rev., vol. 43, (2014), pp. 3666-3761.
Wetz et al., "Quantification of Urinary Timp-2 and igfgp-7: an Adequate Diagnostic Test to Predict Acute Kidney Injury After Cardiac Surgery?," Critical Care, vol. 19, (2015), 7 pages.
Wijeysundera et al., "Derivation And Validation of A Simplified Predictive Index For Renal Replacement Therapy After Cardiac Surgery," JAMA, vol. 297, No. 16, (Apr. 25, 2007), pp. 1801-1809.
Zhu et al., "Relationship Between Urinary Oxygen Tension During Cardiopulmonary Bypass and Development of Acute Kidney Injury," Acta Physiol (Oxf), vol. 227, (2019), 2 pages.
Zhu et al., "Urinary Hypoxia: An Intraoperative Marker Of Risk Of Cardiac Surgey-Associated Acute Kidney Injury," Nephrol Dial Transplant, vol. 33, No. 12, (2018), pp. 1-10.
Anderson, "Continous Real-Time Monitor to Detect Acute Kidney Injury Risk," Patentability Search, (2017), 10 pages.
Bandyopadhyay et al., "A Transeophageal Echocardiology Technique to Locate the Kidney and Monitor Renal Perfusion," Anesth. Analg., vol. 116, (2013), pp. 549-554.
Bellomo et al., "Noradrenaline and the kidney: friends or foes?," Critical Care, vol. 5, No. 6, (2001), pp. 294-298.
Bossard et al., "Early Detection of Postoperative Acute Kidney Injury By Doppler Renal Resistive Index in Cardiac Surgery With Cardiopulmonary Bypass," British Journal of Anaesthesia, vol. 107, No. 6, (2011), pp. 891-898.
Bragadottir et al., "Low-Dose Vasopressin Increases Glomerular Filtration Rate, But Impairs Renal Oxygenation In Post-Cardiac Surgery Patients,", Acta Anestesiol Scand, vol. 53, (2009), pp. 1052-1059.
Bragadottir et al., "Mannitol Increases Renal Blood Flow And Maintains Filtration Fraction And Oxygenation In Postoperative Acute Kidney Injury: A Prospective Interventional Study," Critcal Care, vol. 16, (2012), 9 pages.
Brezis et al., "Hypoxia of The Renal Medulla-Its Implications For Disease," New England Journal of Medicine, vol. 332, No. 10, (Mar. 9, 1995), pp. 647-655.
Chertow et al., "Independent Association Between Acute Renal Failure and Mortality Following Cardiac Surgery", The American Journal of Medicine, vol. 104, (1998), pp. 343-348.
Conlon et al., "Acute Renal Failure Following Cardiac Surgery," Nephrology Dialysis Transplanation, vol. 14, (1999), pp. 1158-1162.
Cummings et al., "Intraoperative Prediction of Cardiac Surgery-Associated Acute Kidney Injury Using Urinary Biomarkers of Cell Cycle Arrest," The Journal of Thoracic and Cardiovascular Surgey, vol. 157, No. 4, (2019), pp. 1545-1554.e5.
Darby et al., "Anernia Increases The Risk of Renal Cortical and Medullary Hypoxia During Cardiopulmonary Bypass," Perfusion, vol. 28, No. 6, (2013), pp. 504-511.
Dyson et al., "Bladder Tissue Oxygen Tension Monitoring in Pigs Subjected to A Range of Cardiorespiratory And Pharmacological Challenges," Intensive Care Med, vol. 38, (2012), pp. 1868-1876.
Elmedany et al., "Novel Urinary Biomarkers And The Early Detection of Acute Kidney Injury After Open Cardiac Surgeries," Journal of Critcal Care, vol. 30, (2017), pp. 171-177.
Endoh et al., "Continuous Intra-Jugular Venous Blood-Gas Monitoring With The Paratrend 7 During Hypothermic Cardiopulmonary Bypass," British Journal of Anaesthesia, vol. 87, No. 2, (2001), pp. 223-228.
Epstein et al., "Oxygen and Renal Metabolism," Kidney International, vol. 51, (1997), pp. 381-385.
Evans et al., "Haernodymanic Influences on Kidney Oxygenation: Clinical Implications of Intergative Physiology," Clin. Exp. Pharmacol. Physiology, vol. 40, (2013), pp. 106-122.
Evans et al., "Stability of Tissue Po2 in The Face of Altered Perfusion: A Phenemenon Specific to The Renal Cortex And Independently Resting Renal Oxygen Consumption," Clinical and Experimental Pharmacology and Physiology, vol. 38, (2011), pp. 247-254.
Evans et al., "Urinary Oxygen Tension: A Clinical Window on The Health of the Renal Medulla?," Am. J. Physiol. Regul. Integr. Comp. Physiology, vol. 306, (2014), pp. R45-R50.

(56) References Cited

OTHER PUBLICATIONS

Finge et al., "Interest of Urinary [TIMP-2]×[IGFBP-7] for Predicting the Occurence of Acute Kidney Injury After Cardiac Surgery: A Gray Zone Approach," Anesth. Analgeisa, vol. 125, No. 3, (2017), pp. 762-769.
Giannakopoulos et al., "Human Bladder Urine Oxygen Content: Implications For Urinary Tract Diseases," Int. Urol. Nephrol, vol. 9, No. 4, (1997), pp. 393-401.
Hori et al., "Defining Oliguria During Cardiopulmonary Bypass And Its Relationship With Cardiac Surgery-Associated Acute Kidney Injury," British Journal of Anaesthesia, vol. 117, No. 6, (2016), pp. 733-740.
Jonannes et al., "Acute Decrease in Renal Microvascular PO2 During Acute Normovolemic Hernodilution," Am. J. Physiol Renal Physiol, vol. 292, (2007), pp. F796-F803.
Kainume et al., "Effect of Acute Changes in Renal Arterial Blood Flow on Urine Oxygen Tension in Dogs," Critcal Care Medicine, vol. 18, No. 3, (1990), pp. 309-312.
Kashani et al., "Discovery And Validation of Cell Cycle Arrest Biomarkers In Human Acute Kidney Injury," Critcal Care, vol. 17, (2013), 12 pages.
Kdigo, "KDIGO Clinical Practice Guideline for Acute Kidney Injury,"Kidney International, vol. 2, (2012), 141 pages.
Kitashiro et al., "Monitoring Urine Oxygen Tension During Acute Change In Cardiac Output In Dogs," J. Appl. Physiol (1985), vol. 79, (1995), pp. 202-204.
Kong et al., "Raman Spectroscopy For Medical Diagnostics—From in-Vitro Biofluid Assays to in-Vivo Cancer Detection," Advanced Drug Delivery Reviews, vol. 89, (2015), pp. 121-134.
Kuitunen et al., "Acute Renal Failure After Cardiac Surgery: Evaulation of the RIFLE Classication," Ann. Thorac Surg. vol. 81, (2006), pp. 542-546.
Lankadeva et al., "Intrarenal And Urinary Oxygenation During Norinephrine Resuscitation In Ovine Septic Acute Kidney Injury," Kidney International, vol. 90, (2016), pp. 100-108.
Lannemyr et al., "Effects of Cardiopulmonary Bypass on Renal Perfusion, Filtration, And Oxygenation in Patients Undergoing Cardiac Surgery," Anesthesiology, vol. 126, No. 2, (2017), pp. 205-213.
Lassen, "Cerebral Blood Flow And Oxygen Consumption In Man," Physiol. Reviews, vol. 39, No. 2, (1959), pp. 183-238.
Leonhardt et al., "Anatomy And Physiology Of Intrarenal Oxygen Tension: Preliminary Study of The Effects of Anesthesitics," Anesthesiology, vol. 26, No. 5, (1965), pp. 648-658.
McLlroy et al., "Incorporating Oliguria Into The Diagnostic Criteria For Acute Kidney Injury After On-Pump Cardiac Surgery: Impact On Incidence And Outcomes," Journal of Cardiothoracic and Vascular Anesthesia, vol. 27, No. 6, (2013), pp. 1145-1152.
Meersch et al., "Urinary TIMP-2 and IGFBP7 as Early Biomarkers of Acute Kidney Injury and Renal Recovery following Cardiac Surgery," PLoS One, vol. 9, No. 3, (2014), 9 pages.

Molnar et al., "Continuous Monitoring Of Scvo(2) By A New Fibre-Optic Technology Compared With Blood Gas Oximetry In Critically Ill Patients: A Multicetre Study," Intensive Care Med, vol. 33, (2007), pp. 1767-1770.
Moyer et al., "Cerebral Hernodynamics During Controlled Hypotension Induced By The Continuous Infusion Of Ganglionic Blocking Agents (Hexamethonium, Pendimide And Arfonad)," J. Clin. Invest, vol. 33, (1954), pp. 1081-1088.
Newland et al., "Low Oxygen Delivery As A Predictor Of Acute Kidney Injury During Cardiopulmonary Bypass," J. Extra Corpor Technology, vol. 49, (2017), pp. 224-230.
Olesen et al., "Elevated Renal Oxygen Extraction During Open Abdominal Aortic Aneurysm Repair Is Releated to Postoperative Renal Dysfunction," Semin Cardiothorac Vasc Anesth, vol. 22, No. 4, (2018), pp. 369-375.
Ostermann et al., "Acute Kidney Injury 2016: Diagnosis and Diagnostic Workup," Critcal Care, vol. 20, (Sep. 27, 2016), 13 pages.
Ranucci et al., "Oxygen Delivery During Cardiopulmonary Bypass And Acute Renal Failure After Coronary Operations," Ann. Thorac Surg, vol. 80, (2005), pp. 2213-2220.
Redfors et al., "Acute Renal Failure Is Not An "Acute Renal Success"—A Clinical Study On The Renal Oxygen Supply/Demand Relationship In Acute Kidney Injury," Critcal Care Med, vol. 38, No. 8, (2010), pp. 1695-1701.
Reents et al., "Acute Kidney Injury After On-Pump or Off-Pump Coronary Artery Bypass Grafting in Elderly Patients," Ann. Thorac Surg, vol. 98, (2014), pp. 9-14.
Reinhart et al., "Continuous Central Venous And Pulmonary Artery Oxygen Saturation Monitoring in the Critically ill," Intensive Care Med, vol. 30, (2004), pp. 1572-1578.
Rennie et al., "Oxygen Pressure in Urine and Its Relation to Intrarenal Blood Flow," Am. J. Physiol, vol. 195, (1958), pp. 120-132.
Sgouralis et al., "Bladder Urine Oxygen Tension For Assessing Renal Medullary Oxygenation In Rabbits: Experimental And Modeling Studies," Am. J. Physiol Regul Integr Comp Physiol, vol. 311, (2016), pp. R532-544.
Sgouralis et al., "Renal Hernodynamics, Function, And Oxygenation During Surgery Performed on Cardiopulmonary Bypass: A Modeling Study," Physiol Rep, vol. 3, (2015), 14 pages.
Sgouralis et al., "Renal Medullary And Urinary Oxygen Tension During Cardiopulmonary Bypass In The Rat," Mathematical Medicine and Biology, vol. 34, (2017), pp. 313-333.
Singh et al., "Renal Oxygenation And Haemodynamics In Acute Kidney Injury And Chronic Kidney Disease," Clin. Exp. Pharmacol Physiol, vol. 40, (2013), pp. 138-147.
Song et al., "Urine Output During Cardiopulmonary Bypass Predicts Acute Kidney Injury After Cardiac Surgery," Medicine, vol. 95, No. 22, (2016), 8 pages.
Stafford-Smith et al., "Renal Medullary Hypoxia During Experimental Cardiopulmonary Bypass: A Pilot Study," Perfusion, vol. 20, (2005), pp. 53-58.

\* cited by examiner

CATHETER ASSEMBLIES, OXYGEN-SENSING ASSEMBLIES, AND RELATED METHODS

CROSS-REFERENCE TO RELATED APPLICATION

This application claims the benefit under 35 U.S.C. § 119(e) of U.S. Provisional Patent Application Ser. No. 62/555,161, filed Sep. 7, 2017, the disclosure of which is hereby incorporated herein in its entirety by this reference.

FIELD

Embodiments of the present disclosure relate generally to urinary catheter assemblies and oxygen-sensing assemblies. Additionally, embodiments of the present disclosure relate generally to measuring oxygen tension within fluids and determining risk of acute kidney injury (e.g., urinary hypoxia) in patients.

BACKGROUND

Acute kidney injury (hereinafter "AKI") is an unfortunately common complication of cardiac surgery that occurs in up to 40% of patients and results in increased mortality, prolonged intensive care unit stays, and prolonged hospital stays. Patients with AKI after cardiac surgery have been shown to have 39 times the mortality rate as patients without AKI. AKI has also been associated with increased morbidity and a larger number of patients requiring discharge to an extended care facility.

Conventionally, diagnosing AKI has been based on either a sustained decrease in urine output or a rise in serum creatinine. A major limitation of utilizing serum creatinine levels and urine output as markers of kidney function and renal injury is that there is a significant time lag between an actual injury and diagnosis. For instance, it often takes 24 to 36 hours after renal injury for serum creatinine levels to increase. As a result, diagnosis of AKI via the foregoing method is delayed by at least 24 to 36 hours. Additionally, perioperative urine output is affected by volume status, anesthetic drugs, and the use of diuretics, and AKI is typically not diagnosed until oliguria has occurred for at least 6 to 12 hours. Accordingly, the inherent time lags in measuring serum creatinine and an uncertainties in measuring urinary output render the measurements insensitive to acute changes in renal function and relatively useless in the prevention of AKI during and after cardiac surgery.

More recently, several early biomarkers have been developed to identify patients whom are at risk for developing AKI. Several of these biomarkers have been used for the early prediction of AKI in cardiac surgery patients. However, even these biomarkers still do not indicate AKI until at least 3 to 4 hours (and in some cases, 24 hours) after renal injury.

Accordingly, one of the major limitations in the efforts to reduce the incidence of AKI in cardiac surgery is the lack of a real-time monitor of renal perfusion. As mentioned above, urine output is well known to be a poor indicator of renal perfusion. While urinary flowrate may be linearly related to blood pressure while on a cardiopulmonary bypass ("CPB"), this is likely related to a phenomenon called "pressure diuresis" and is unlikely to be a reflection of improved renal perfusion. Renal blood flow can be measured by cannulating the renal vein through a central venous catheter placed in the femoral vein. This, however, is a highly invasive technique and is not utilized routinely.

As a result of the lack of real-time monitoring of the kidneys during cardiac surgery, anesthesiologists are often left to make educated guesses as to which blood pressures and cardiac outputs are adequate for renal perfusion based on the patient's baseline blood pressure and kidney function. In a patient with a long history of hypertension and/or chronic kidney disease the anesthesiologist's goal is often to try to maintain a higher mean arterial pressure (MAP) both on and off CPB than normal in order to improve renal perfusion.

Medullary hypoxia may be a consequence of decreased oxygen delivery or increased oxygen consumption and is a major determinant of AKI and chronic kidney disease. The relatively hypoxic environment of the renal medulla and its role in renal injury suggests that global measures of systemic venous oxygenation through a central venous catheter or even renal venous oxygenation through an invasive renal vein catheter may be poor monitors of adequate renal perfusion. Due to the physical proximity of the vasa *recta* in the renal medulla with the urinary collecting ducts, medullary oxygen tension is more closely related to urinary oxygen tension than renal venous oxygenation.

Accordingly, these and other disadvantages exist with respect to conventional methods and systems for diagnosing AKI in cardiac surgery patients.

BRIEF SUMMARY

Some embodiments of the present disclosure include a catheter assembly, including a urinary catheter, an oxygen-sensing assembly, and a control system. The urinary catheter may include a lumen extending between an inlet end and an outlet end thereof. The oxygen-sensing assembly may be in fluid communication with the urinary catheter. The oxygen-sensing assembly may include a housing having a flow pathway extending between an inlet end and an outlet end thereof, wherein the inlet end of the housing is attachable to the outlet end of the urinary catheter, an oxygen sensor in operable communication with the flow pathway of the housing, the oxygen sensor configured to detect oxygen levels of a fluid flowing through the flow pathway, a flowrate sensor disposed between the oxygen sensor and the inlet end of the housing and configured to detect a flowrate of the fluid flowing through the flow pathway, and a temperature sensor disposed downstream of the oxygen sensor and configured to detect a temperature of the fluid flowing through the flow pathway. The control system may be operably coupled to the oxygen sensor, the flowrate sensor, and the temperature sensor. The control system may include at least one processor and at least one non-transitory computer-readable storage medium storing instructions thereon that, when executed by the at least one processor, cause the control system to: receive a detected and/or calculated oxygen levels, a detected and/or calculated flowrate, and a detected temperature of the fluid flowing through the flow pathway and based at least partially on one or more of the detected oxygen levels and the detected temperature, determine a measurement of an oxygen tension of the fluid flowing through the flow pathway of the housing.

One or more embodiments of the present disclosure includes an oxygen-sensing assembly for attachment to a urinary catheter. The oxygen-sensing assembly may include a housing having a flow pathway extending between an inlet end and an outlet end thereof and an oxygen sensor in operable communication with the flow pathway of the housing, the oxygen sensor configured to detect oxygen levels of a fluid in or flowing through the flow pathway.

Some embodiments of the present disclosure include a method that includes attaching an oxygen-sensing assembly to a urinary catheter; disposing the urinary catheter within a bladder of a subject; detecting oxygen levels of a fluid flowing through the urinary catheter and through a flow pathway of a housing of the oxygen-sensing assembly with an oxygen sensor; detecting a flowrate of the fluid flowing through the flow pathway with a flowrate sensor; detecting a temperature of the fluid flowing through the flow pathway with a temperature sensor; and based at least partially on one or more of the detected and/or calculated oxygen levels and the detected and/or calculated temperature of the fluid, determining a measurement of an oxygen tension of the fluid flowing through the flow pathway.

DETAILED DESCRIPTION

Figure 1:
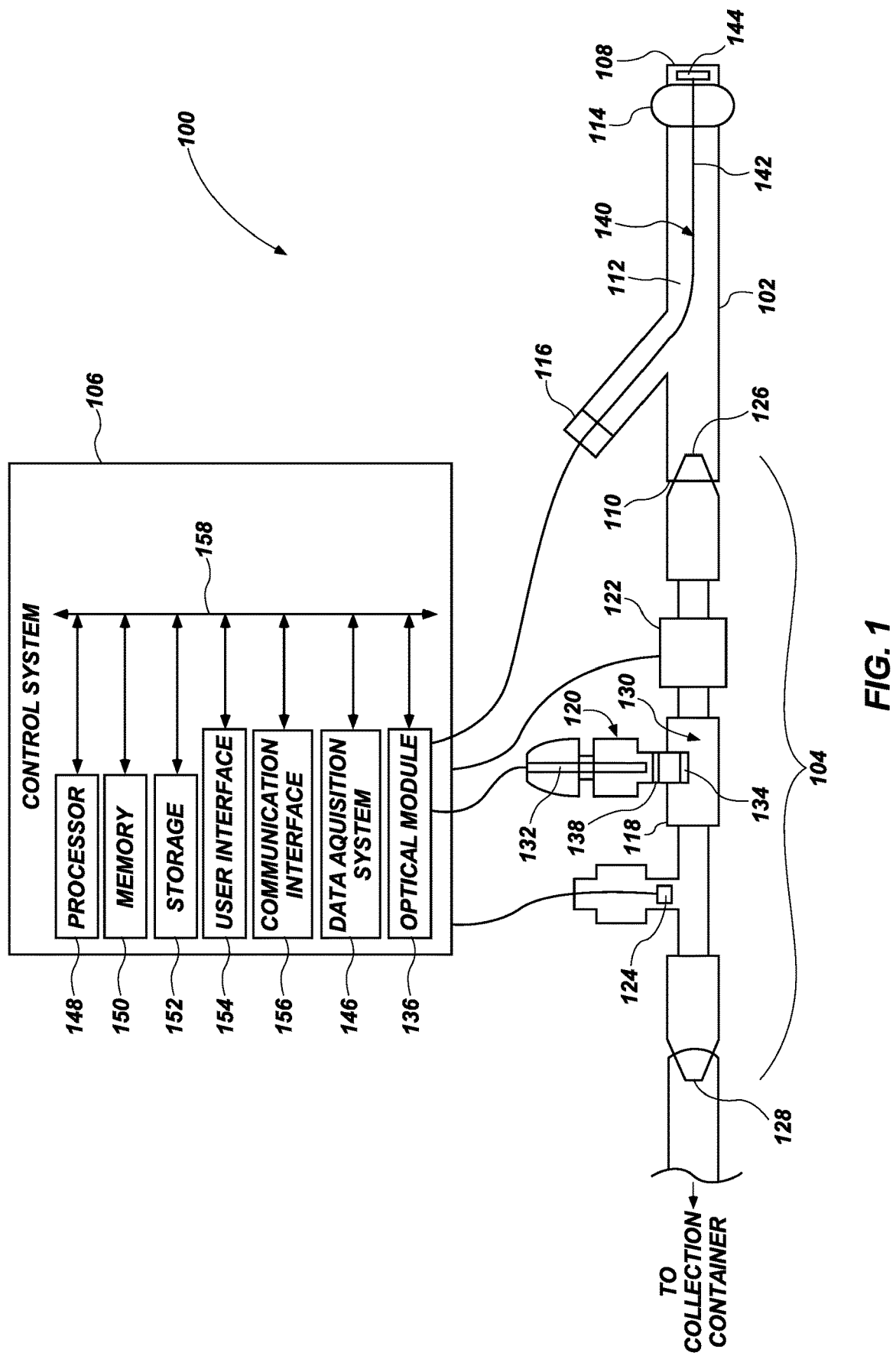
FIG. 1 is a schematic representation of a catheter assembly having an oxygen-sensing assembly according to one or more embodiments of the present disclosure.

The illustrations presented herein are not actual views of any particular catheter assembly, but are merely idealized representations employed to describe example embodiments of the present disclosure. The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. Also note, any drawings accompanying the application are for illustrative purposes only, and are thus not drawn to scale. Additionally, elements common between figures may have corresponding numerical designations.

As used herein, the terms "comprising," "including," and grammatical equivalents thereof are inclusive or open-ended terms that do not exclude additional, un-recited elements or method steps, but also include the more restrictive terms "consisting of," "consisting essentially of," and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "below," "lower," "bottom," "above," "upper," "top," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, the spatially relative terms may refer to a catheter assembly when the catheter is placed in a patient.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

FIG. 1 shows a catheter assembly 100 according to one or more embodiments of the present disclosure. The catheter assembly 100 may include a urinary catheter 102, an oxygen-sensing assembly 104 in fluid communication with the urinary catheter 102, and a control system 106 operably coupled to the oxygen-sensing assembly 104.

The urinary catheter 102 may include an inlet end 108, an outlet end 110, and a lumen 112 extending between the inlet end 108 and the outlet end 110. In some embodiments, the urinary catheter 102 may include a Foley catheter. For instance, the urinary catheter 102 may include a flexible tube that may be passed (e.g., inserted) through the urethra of a patient and into the bladder of the patient in order to drain urine. Furthermore, in some embodiments, the urinary catheter 102 and the oxygen-sensing assembly 104 may form a single integral unit. As will be appreciated by one of ordinary skill in the art, the urinary catheter 102 may further include a balloon 114 proximate the inlet end 108 that can be inflated with sterile water once the urinary catheter 102 has been placed and when the balloon 114 lies within the bladder of the patient. The balloon 114 may prevent the urinary catheter 102 from slipping out of the bladder of the patient. Additionally, the urinary catheter 102 may include a balloon port 116 for inflating the balloon 114. As will be described in greater detail below, in some embodiments of the present disclosure, the urinary catheter 102 may include one or more additional lumens that may provide an access port for one or more oxygen sensors of the present disclosure.

As noted above, the oxygen-sensing assembly 104 may be in fluid communication with the urinary catheter 102 and may include a housing 118, an oxygen sensor 120, a flowrate sensor 122, and a temperature sensor 124. The housing 118 may include an inlet end 126 and an outlet end 128 and may define a flow pathway 130 between the inlet end 126 and the outlet end 128. The inlet end 126 of the housing 118 may be attachable to the outlet end 110 of the urinary catheter 102 via any connection methods known in the art. The oxygen sensor 120, the flowrate sensor 122, and the temperature sensor 124 may be disposed along the flow pathway 130 in series. Furthermore, although a specific component order is illustrated in FIG. 1, the disclosure is not so limited, and the oxygen sensor 120, the flowrate sensor 122, and the temperature sensor 124 may be positioned in any order. Moreover, in one or more embodiments, one or more of the oxygen sensor 120, the flowrate sensor 122, and the temperature sensor 124 may be positioned in parallel with another of the oxygen sensor 120, the flowrate sensor 122, and the temperature sensor 124. Additionally, in some embodiments, one or more of the oxygen sensor 120, the flowrate sensor 122, and the temperature sensor 124 may be combined into a single sensor.

In some embodiments, the flowrate sensor 122 may include a liquid flow meter. For instance, the flowrate sensor 122 may detect and determine a flowrate of a fluid (e.g., urine) through the flow pathway 130 of the oxygen-sensing assembly 104. Many such flowrate sensors are known in the art, and the flowrate sensor 122 may comprise any of the flow sensors known in the art. Furthermore, the flowrate sensor 122 may be operably coupled to the control system 106 and may provide data related to a flowrate of the fluid through the flow pathway 130 to the control system 106. For instance, as is described in greater detail below, the control system 106 may utilize data from the flowrate sensor 122 to assist in qualifying an oxygen tension (PuO2) measurement within urine through the flow pathway 130 (i.e., determine whether the oxygen tension (PuO2) measurement is relevant to bladder and/or kidney oxygen tensions), to determine a risk of acute kidney injury (e.g., urinary hypoxia) of a patient. Additionally, the control system 106 may utilize data from the flowrate sensor 122 to determine (e.g., back calculate) an oxygen tension (PuO2) measurement of the bladder and/or kidney of the patient. For instance, the control system 106 utilizes the flowrate sensor 122 to determine how long the urine has been out of the bladder and/or kidneys of the patient prior to being measured with the oxygen sensor 120 and/or temperature sensor 124. In one or more embodiments, the flowrate sensor 122 may be positioned downstream of the oxygen sensor 120 along the flow pathway 130 of the oxygen-sensing assembly 104. Furthermore, in some instance, the flowrate sensor 122 may heat urine passing through flowrate sensor 122. As a result, disposing the flowrate sensor 122 downstream of the oxygen sensor 120 may be advantageous in order to avoid having the oxygen sensor 120 measuring heated urine. Furthermore, having oxygen sensing upstream, or closer to an outlet end 110 of the urinary catheter 102 may be advantageous because oxygen sensing upstream shortens a path that the urine must travel from a kidney to a sensor (e.g., the oxygen sensor 120). As a result, the oxygen sensing methods described herein shorten a lag between the sensor's readings and what is actually occurring within the kidney. In other embodiments, the flowrate sensor 122 may be positioned upstream of the oxygen sensor 120 along the flow pathway 130 of the oxygen-sensing assembly 104.

In one or more embodiments, the oxygen sensor 120 may be at least partially disposed within the flow pathway 130 of the oxygen-sensing assembly 104. Furthermore, the oxygen sensor 120 may detect oxygen levels within urine passing through (i.e., flowing through) the flow pathway 130 of the oxygen-sensing assembly 104. In some embodiments, the oxygen sensor 120 may include a fiber optic sensor. For instance, the oxygen sensor 120 may include an optical fiber 132 and a sensing portion 134. As a non-limiting example, the oxygen sensor 120 may include a Fiber Bragg grating sensor. The optical fiber 132 may be operably coupled to an optical module 136 of the control system 106 and may extend at least partially into the housing 118 of the oxygen-sensing assembly 104. The sensing portion 134 may be disposed at least partially within the flow pathway 130 of the oxygen-sensing assembly 104 and may be exposed to the fluid (e.g., urine) flowing through the flow pathway 130 of the oxygen-sensing assembly 104.

In some embodiments, the sensing portion 134 of the oxygen sensor 120 may be secured to a distal end of the optical fiber 132. In other embodiments, the sensing portion 134 of the oxygen sensor 120 may be separated from the optical fiber 132 (e.g., may be separate and distinct from the optical fiber 132). In embodiments where the sensing portion 134 of the oxygen sensor 120 is separate and distinct from the optical fiber 132, the oxygen sensor 120 may include a barrier member 138 (e.g., a polymer wall) between the sensing portion 134 and the optical fiber 132. The barrier member 138 may prevent the optical fiber 132 from coming into contact with (e.g., being contaminated by) the fluid (e.g., urine) flowing through the flow pathway 130 of the housing 118 of the oxygen-sensing assembly 104. As a result, use of the barrier member 138 enables the optical fiber 132 to be reusable with other oxygen-sensing assemblies. In further embodiments, the oxygen sensor 120 may not include an optical fiber 132 and the oxygen-sensing assembly 104 may emit light from and may detect light at the sensing portion 134. The structure of the oxygen sensor 120 is described in greater detail in below in regard to FIG. 2.

As will be appreciated by one of ordinary skill in the art, in operation, the optical fiber 132 of the oxygen sensor 120 may transmit light (e.g., excitation light) from the optical module 136 of the control system 106 (e.g., emitted and/or generated by the optical module 136) through a distal end of the optical fiber 132 and at (i.e., toward) the sensing portion 134 of the oxygen sensor 120. Additionally, the optical fiber 132 may transmit light (e.g., return light) emitted and/or reflected by (e.g., light originated at) the sensing portion 134 of the oxygen sensor 120 through the distal end of the optical fiber 132 and may transmit the return light back to the optical module 136 and control system 106 for analysis.

In some embodiments, the optical fiber 132 may include a core and a cladding, which is known in the art. For example, the optical fiber 132 may include a single mode fiber, a multi-mode fiber, or special-purpose fiber (e.g., an optical fiber constructed with a non-cylindrical core and/or cladding layer). Furthermore, the optical fiber 132 may include one or more of a step-index multi-mode fiber, a graded-index multimode fiber, a loose-tube cable, or a tight-buffered cable. In one or more embodiments, the core of the optical fiber 132 may include one or more of silica, fluorozirconate glass, fluoroaluminate glass, chalcogenide glass, fluoride glass, phosphate glass, poly(methyl methacrylate), or polystyrene. Additionally, the cladding of the optical fiber 132 may include fluorinated polymers. For example, the optical fiber 132 may include any optical fiber known in the art.

In some embodiments, the sensing portion 134 may include a dye-impregnated polymer or silica impregnated with fluorescent dyes, which dyes are excitable at selected wavelengths of light. In one or more embodiments, the dyes may be oxygen sensitive and may be immobilized (e.g., impregnated) within a polymer matrix. For example, the dyes may be sensitive to oxygen such that the oxygen quenches a fluorescence response of the dyes. Additionally, in some embodiments, the polymer or silica may be applied to a carrier material such as a foil and may be separate from the optical fiber 132. Moreover, as noted above, in some embodiments, the polymer may be coated directly onto the optical fiber 132. As a non-limiting example, the sensing portion 134 may include any fluorescence quenching oxygen sensor known in the art.

In some embodiments, the dye of the sensing portion 134 may include one or more of a platinum(II) based dye, a palladium(II) based dye, a ruthenium(II) based dye, or a hemoglobin based dye. For example, the dye may include platinum octaethylporphyrin. Furthermore, the sensing portion 134 may include any other dyes known in the art.

In operation, the optical fiber 132 may transmit excitation light from the optical module 136 of the control system 106 to the sensing portion 134 of the oxygen sensor 120, which is exposed to urine and any oxygen molecules within the urine. Additionally, simultaneously, the optical fiber 132 may transmit a fluorescence response (i.e., emission of light by a substance not resulting from heat and a form of cold-body radiation) of the sensing portion 134 (e.g., return light) to the optical module 136 of the control system 106 for analysis. Furthermore, depending on the amount of oxygen molecules that are (e.g., an oxygen concentration) present in the urine flowing through the flow pathway 130 of the oxygen-sensing assembly 104, the luminescence response (e.g., the return light) of the sensing portion 134 may vary. For instance, the fluorescence response may be quenched by the presence of the oxygen molecules. In other words, the fluorescence response of the sensing portion 134 may decrease as a concentration of oxygen increases within the fluid. In additional embodiments, the luminescence response may include amplitudes of the fluorescent response.

As a non-limiting example, in some embodiments, the optical module 136 of the control system 106 may provide (e.g., generate) a sinusoidally modulated excitation light (e.g., an excitation beam having a wavelength of about 432 nm). Furthermore, shining the foregoing excitation light on the sensing portion 134 of the oxygen sensor 120 may result in a phase-shifted sinusoidally modulated return light (e.g., a return beam having a wavelength of about 760 nm). As is discussed in greater detail in regard to FIG. 3, upon receiving the return light through the optical module 136, the control system 106 may measure a phase shift of the phase-shifted sinusoidally modulated return light relative to the sinusoidally modulated excitation light. Furthermore, the control system 106 may determine oxygen levels of the fluid (e.g., concentrations of oxygen within the fluid) based on the phase shift and based on the Stern-Vollmer-Theory. For instance, control system 106 may determine oxygen levels of the fluid based on the phase shift of the return light utilizing the following Stern-Vollmer Equation:

$$\frac{F_0}{F} = 1 + K_{SV}[Q]$$

where $F_0$ and $F$ represent the fluorescence intensities observed in the absence (e.g., sinusoidally modulated excitation light) and in the presence (e.g., phase-shifted sinusoidally modulated return light) of a quencher. [Q] represents a quencher concentration (e.g., oxygen concentration) and $K_{SV}$ represents the Stern-Vollmer quenching constant. The operation of the oxygen sensor 120 is described in greater detail in regard to FIGS. 2 and 3.

Referring still to FIG. 1, in some embodiments, the oxygen sensor 120 may include an electrochemical oxygen sensor. For instance, the oxygen sensor 120 may include a polarographic sensor. As a non-limiting example, the oxygen sensor 120 may include a Clark electrode, which measures ambient oxygen concentration within a liquid using a catalytic platinum surface according to the following net reaction:

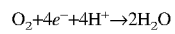

$$O_2 + 4e^- + 4H^+ \rightarrow 2H_2O$$

In additional embodiments, the oxygen sensor 120 may include a pulsed polarographic sensor. In further embodiments, the oxygen sensor 120 may include a galvanic sensor (e.g., an electro-galvanic fuel cell), as is known in the art.

In additional embodiments, the oxygen sensor 120 may include a colorimetric oxygen sensor. For example, the oxygen sensor 120 may utilize the Indigo Carmine Method (as known in the art) to determine oxygen levels within the fluid flowing through the flow pathway 130 of the housing 118 of the oxygen-sensing assembly 104. In further embodiments, the oxygen sensor 120 may utilize the Rhodazine Method (as known in the art) to determine oxygen levels within the fluid.

Regardless of the type of oxygen sensor utilized, the oxygen sensor 120, in conjunction with the control system 106, may be used to detect and determine a concentration of oxygen (e.g., an amount of oxygen per volume of fluid) within the fluid (e.g., urine) flowing through the flow pathway 130 of the oxygen-sensing assembly 104. For instance, utilizing the oxygen sensor 120, the control system 106 may determine a partial pressure of oxygen, a dissolved oxygen concentration, a head space oxygen gas concentration, a dissolved oxygen reading, etc., of the fluid. Furthermore, the control system 106 may determine oxygen levels within the fluid in real-time.

Referring still to FIG. 1, in some embodiments, the temperature sensor 124 may be downstream of the oxygen sensor 120 along the flow pathway 130 of the oxygen-sensing assembly 104. In other embodiments, the temperature sensor 124 may be positioned upstream of the oxygen sensor 120. In some embodiments, having the temperature sensor 124 downstream of the oxygen sensor 120 may be advantageous as it may enable determining that a temperature of the urine passing by the oxygen sensor 120 is within a range of a body temperature of the patient and a temperature of the urine measured with the temperature sensor 124. Furthermore, in one or more embodiments, the temperature sensor 124 may be directly adjacent to the oxygen sensor 120. The foregoing configuration may increase accuracy of measurements. In one or more embodiments, the temperature sensor 124 may include a thermistor. For example, the temperature sensor 124 may include a negative temperature coefficient ("NTC") thermistor. For instance, the temperature sensor 124 may include a temperature-sensing element including a semiconductor material that is sintered to display large changes in resistance in proportion to small changes in temperature. In further embodiments, the temperature sensor 124 may be integrated with the flowrate sensor 122.

In some embodiments, the temperature sensor 124 may not be in contact with the fluid (e.g., urine) flowing through the flow pathway 130 of the oxygen-sensing assembly 104. For example, the temperature sensor 124 may include a non-contact sensor that compensates for material (e.g., a wall) between the temperature sensor 124 and the fluid of which the temperature sensor 124 is detecting temperature. For instance, the control system 106 may adjust any detected temperature value to compensate for a temperature loss across the material separating the temperature sensor 124 and the fluid. Furthermore, the control system 106 may utilize a temperature difference between what is measured with the temperature sensor 124 and a temperature measured at a tip of the urinary catheter 102 to determine and compensate for temperature losses or gains while flowing through the catheter assembly 100. In other embodiments, the temperature sensor 124 may be positioned to come in contact with the fluid (e.g., urine) flowing through the flow pathway 130 of the oxygen-sensing assembly 104. For instance, the temperature sensor 124 may access the flow pathway 130 of the oxygen-sensing assembly 104 via a Tuohy-Borst clamp.

In further embodiments, the catheter assembly 100 may include a heating element and/or a cooling element for actively heat and/or cool urine passing through flow pathway 130 of the oxygen-sensing assembly 104 and for maintaining a temperature of the urine throughout at least a portion of the catheter assembly 100. In some embodiments, the catheter assembly 100 may include at least one heating wire within the catheter assembly 100 (e.g., within the flow pathway of the oxygen-sensing assembly 104) for heating the urine. In additional embodiments, the catheter assembly 100 may include one or more thermoelectric coolers disposed within or around portions of the catheter assembly for cooling the urine. For instance, the catheter assembly 100 may include one or more conventional thermoelectric coolers. Maintaining a temperature of the urine with at least a portion of the catheter assembly 100 may provide more consistent and accurate oxygen measurements, as described below.

Furthermore, the temperature sensor 124 may be operably coupled to the control system 106 and may provide data related to a detected temperature of the fluid flowing through the flow pathway 130 of the oxygen-sensing assembly 104 to the control system 106. As is described in greater detail in regard to FIG. 3, the control system 106 may utilize the data related to the detected temperature of the fluid to adjust determined oxygen levels determined via the oxygen sensor 120. For instance, the control system 106 may adjust determined oxygen levels based on the detected temperature utilizing Henry's Law combined with Van't Hoff's equation, as follows:

$$Conc_{Dissolved\ Oxygen} = p_{O_2\ Gas} \times k_H(298.15\ K) \times e^{C_{O_2} \times \left(\frac{1}{T} - \frac{1}{298.15K}\right)}$$

Referring still to FIG. 1, the outlet end 128 of the oxygen-sensing assembly 104 may be attachable to a fluid collection container (e.g., a urine collection bag).

Additionally, in one or more embodiments, the oxygen-sensing assembly 104 may include an additional oxygen sensor 140 (i.e., a second oxygen sensor). The additional oxygen sensor 140 may extend through the balloon port 116 of the urinary catheter 102 and into the lumen 112 of the urinary catheter 102. Moreover, the additional oxygen sensor 140 may include any of the oxygen sensor types described above in regard to oxygen sensor 120 (i.e., the first oxygen sensor). For instance, the additional oxygen sensor 140 may include an optical fiber 142 and a sensing portion 144. The sensing portion 144 of the additional oxygen sensor 140 may be disposed within the lumen 112 of the urinary catheter 102 in order to detect oxygen levels of a fluid (e.g., urine) in the bladder of the patient without extending out of the lumen 112 (e.g., the inlet end 108) of the urinary catheter 102. As a non-limiting example, the sensing portion 144 of the additional oxygen sensor 140 may be secured to the optical fiber 142 of the additional oxygen sensor 140, as described above in regard to oxygen sensor 120. Furthermore, the additional oxygen sensor 140 may operate and function via any of the manners described above in regard to oxygen sensor 120. Additionally, the additional oxygen sensor 140 may be operably coupled to the optical module 136 of the control system 106. Because the oxygen-sensing assembly 104 includes two separate oxygen sensors, the control system 106 may acquire two separate oxygen readings. As a result, the oxygen-sensing assembly 104 may provide more accurate oxygen readings in comparison to a single oxygen sensor.

One will appreciate that one or more computing device components may be employed to implement the control system 106. The control system 106 may include the optical module 136, a data acquisition system 146, a processor 148, a memory 150, a storage device 152, a user interface 154, and a communication interface 156, which may be communicatively coupled by way of a communication infrastructure 158. While one example of a computing device is shown in FIG. 1, the components illustrated in FIG. 1 are not intended to be limiting. Additional or alternative components may be used in other embodiments. Furthermore, in certain embodiments, the control system 106 may include fewer components than those shown in FIG. 1. Components of the control system 106 shown in FIG. 1 are described in additional detail below.

In one or more embodiments, the optical module 136 may provide (e.g., generate) light (e.g., excitation beams) for the oxygen sensor 120 and additional oxygen sensor 140. Furthermore, the optical module 136 may receive return light from the sensing portions 134, 144 of the oxygen sensor 120 and the additional oxygen sensor 140. Moreover, the optical module 136 may convert any received light into data and may provide the data to the data acquisition system 146 of the control system 106. As noted above, in some embodiments, the optical module 136 may be disposed at and/or within the sensing portions 134, 144 of the oxygen sensor 120 and the additional oxygen sensor 140 removing any need for an optical fiber. As a non-limiting example, the optical module 136 may comprise any suitable optical module known in the art.

The data acquisition system 146 may receive signals from one or more of the optical module 136, temperature sensor 124, flowrate sensor 122, oxygen sensor 120, and/or additional oxygen sensor 140 and may include, or have associated therewith, analog to digital conversion circuitry to convert the analog signals from the optical module and the various sensors into digital numeric values that can be manipulated and/or analyzed by the control system 106 (e.g., the processor 148 and/or the data acquisition system 146 of the control system 106). The data acquisition system 146 may further include one or more software programs developed using various general purpose programming languages such as Assembly, BASIC, C, C++, C#, Fortran, Java, LabVIEW, Lisp, Pascal, etc. As a non-limiting example, the control system 106 may include any data acquisition system known in the art.

In one or more embodiments, the processor 148 includes hardware for executing instructions, such as those making up a computer program. As an example and not by way of limitation, to execute instructions, the processor 148 may retrieve (or fetch) the instructions from an internal register, an internal cache, the memory 150, or the storage device 152 and decode and execute them. In one or more embodiments, the processor 148 may include one or more internal caches for data, instructions, or addresses. As an example and not by way of limitation, the processor 148 may include one or more instruction caches, one or more data caches, and one or more translation lookaside buffers (TLBs). Instructions in the instruction caches may be copies of instructions in the memory 150 or the storage 152.

Figure 2:
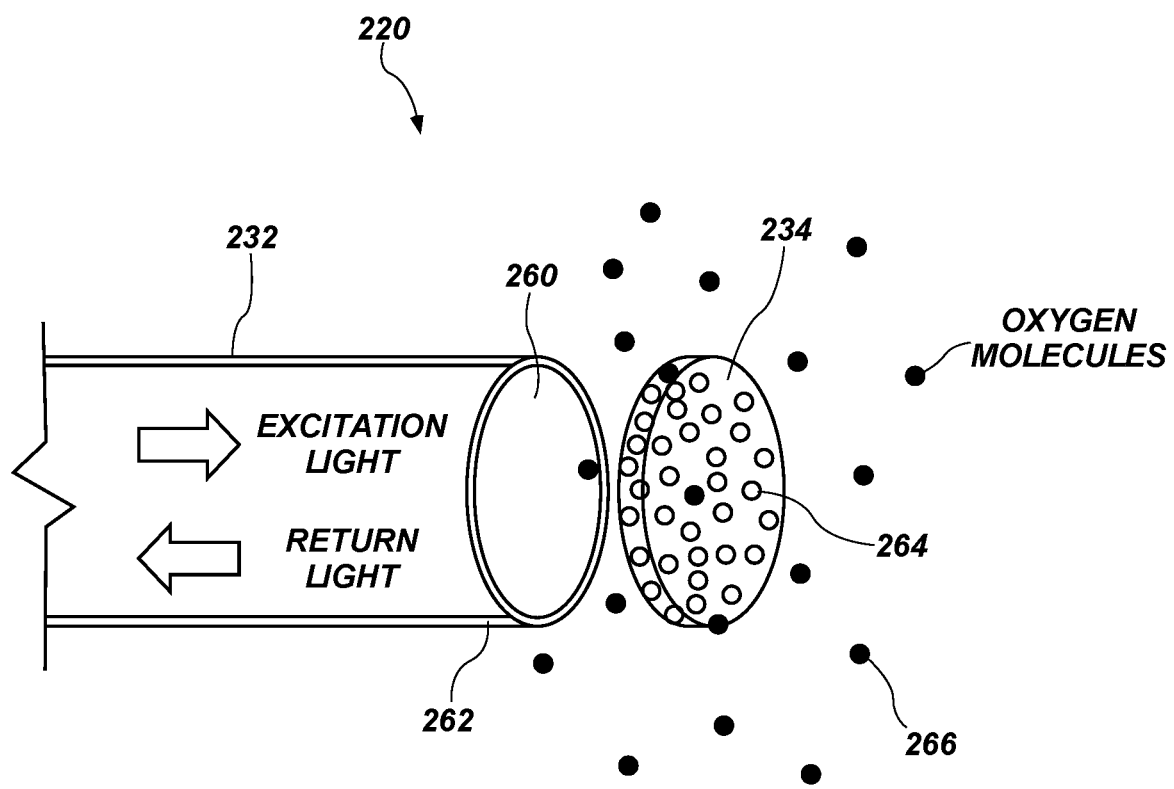
FIG. 2 is a schematic representation of an oxygen sensor according to one or more embodiments of the present disclosure.
Figure 3:
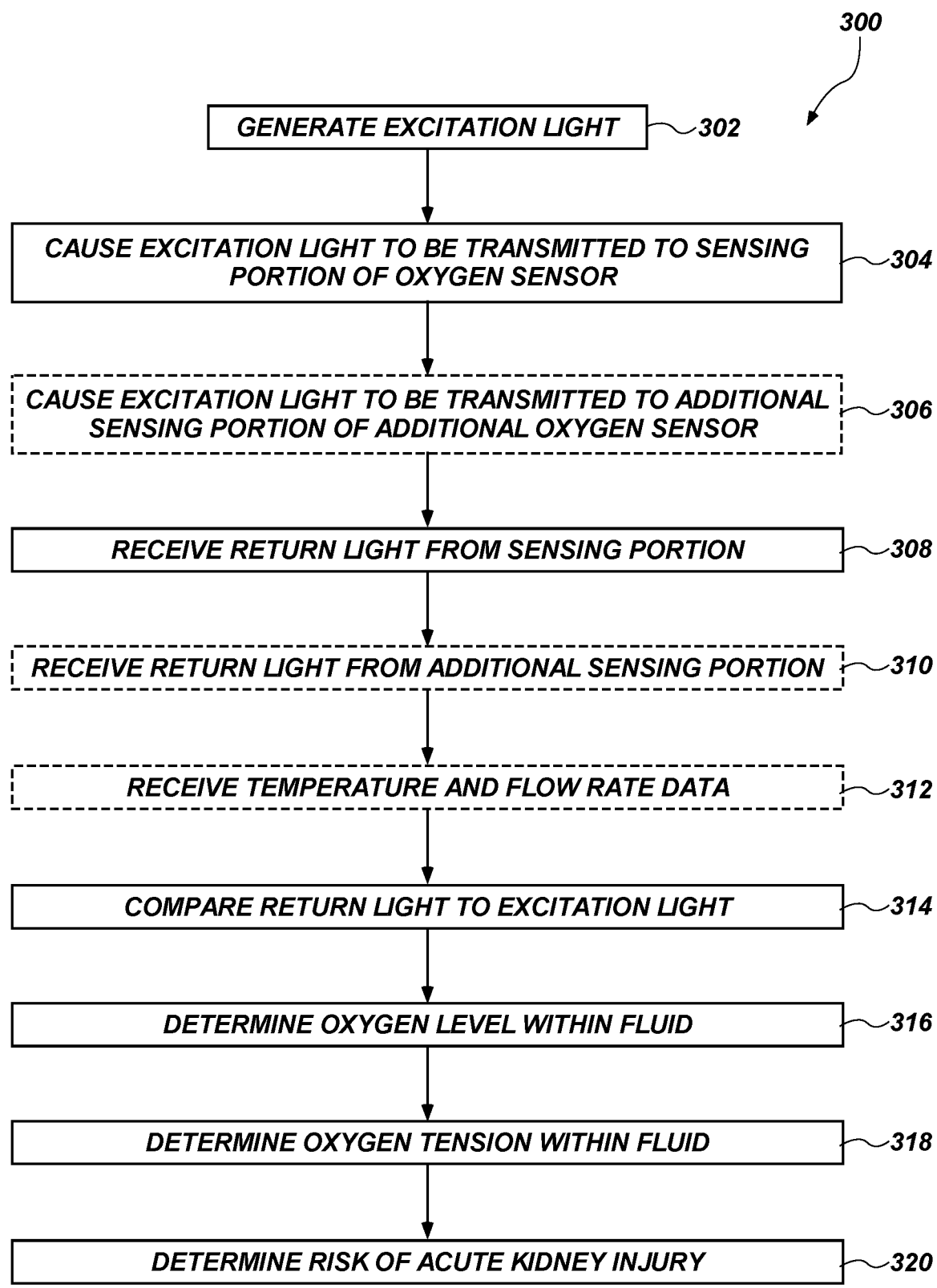
FIG. 3 is a flow diagram illustrating a method flow that a catheter assembly may utilize to determine oxygen tension within urine of a patient.

As is described in greater detail in regard to FIGS. 2 and 3, the control system 106 may utilize the optical module 136, data acquisition system 146, and the processor 148 to determine urine oxygen tension within the urine flowing through the flow pathway 130 of the oxygen-sensing assembly 104 based at least partially on one or more of the detected oxygen levels of the urine, the detected temperature of the urine, or the detected flowrate of the urine. Furthermore, based on the determined urine oxygen tension, the control system 106 may determine a risk of developing acute kidney injury (e.g., urinary hypoxia) in a patient. For instance, the control system 106 may diagnose kidney hypoxia.

The memory 150 may be used for storing data, metadata, and programs for execution by the processor(s). The memory 150 may include one or more of volatile and non-volatile memories, such as Random Access Memory ("RAM"), Read Only Memory ("ROM"), a solid state disk ("SSD"), Flash, Phase Change Memory ("PCM"), or other types of data storage. The memory 150 may be internal or distributed memory.

The storage device 152 includes storage for storing data or instructions. As an example and not by way of limitation, storage device 152 can comprise a non-transitory storage medium described above. The storage device 152 may include a hard disk drive (HDD), a floppy disk drive, flash memory, an optical disc, a magneto-optical disc, magnetic tape, a Universal Serial Bus (USB) drive or a combination of two or more of these. The storage device 152 may include removable or non-removable (or fixed) media, where appropriate. The storage device 152 may be internal or external to the control system 106. In one or more embodiments, the storage device 152 is non-volatile, solid-state memory. In other embodiments, the storage device 152 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The user interface 154 allows a user to provide input to, receive output from, and otherwise transfer data to and receive data from control system 106. The user interface 154 may include a mouse, a keypad or a keyboard, a touch screen, a camera, an optical scanner, network interface, modem, other known user devices or a combination of such user interfaces. The user interface 154 may include one or more devices for presenting output to a user, including, but not limited to, a graphics engine, a display (e.g., a display screen), one or more output drivers (e.g., display drivers), one or more audio speakers, and one or more audio drivers. In certain embodiments, the user interface 154 is configured to provide graphical data to a display for presentation to a user. The graphical data may be representative of one or more graphical user interfaces and/or any other graphical content as may serve a particular implementation.

The communication interface 156 may include hardware, software, or both. In any event, the communication interface 156 is configured to provide one or more interfaces for communication (such as, for example, packet-based communication) between the control system 106 and one or more other computing devices or networks. As an example and not by way of limitation, the communication interface 156 may include a network interface controller (NIC) or network adapter for communicating with an Ethernet or other wire-based network or a wireless NIC (WNIC) or wireless adapter for communicating with a wireless network, such as a WI-FI.

Additionally or alternatively, the communication interface 156 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the communication interface 156 may facilitate communications with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof.

Additionally, the communication interface 156 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), user Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 158 may include hardware, software, or both that couples components of the control system 106 to each other. As an example and not by way of limitation, the communication infrastructure 158 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

Referring still to FIG. 1, in one or more embodiments, the oxygen-sensing assembly 104 may further include one or more valves (e.g., check valves) for directing fluid flow through the flow pathway 130 of the oxygen-sensing assembly 104. As will be appreciated by one of ordinary skill in the art, including one or more valves for directing fluid flow through the flow pathway 130 of the oxygen-sensing assembly 104 may prevent backflow and may reduce infection risks, and as a result, may decrease sickness and disease that may be caused by contamination and infection attributable to use of the disclosed embodiments. For instance, in embodiments where the of the oxygen-sensing assembly 104 includes a relatively larger lumen, a check valve may be useful to prevent pockets of air from moving up tubing extending to the fluid collection container and contaminating the oxygen sensor 120 with oxygen. In embodiments utilizing a relatively small lumen, the foregoing problem is eliminated as the lumen allows a surface tension of the urine to prevent encroachment of bubbles.

FIG. 2 is a partial schematic representation of an oxygen sensor 220 according to one or more embodiments of the present disclosure. The oxygen sensor 220 of FIG. 2 may be utilized as either the oxygen sensor 120 or the additional oxygen sensor 140 described in regard to FIG. 1. In some embodiments, the oxygen sensor 220 may include an optical fiber 232 and a sensing portion 234. As described above, the optical fiber 232 may include a core 260 and a cladding 262 and may be operable coupled to the optical module 136 (FIG. 1) of the control system (FIG. 1). Additionally, the optical fiber 232 may transmit excitation light in a first direction (e.g., toward a distal end of the optical fiber 232 and the sensing portion 234) and return light in a second opposite direction (e.g., toward the optical module 136 of the control system 106 and from the sensing portion 234).

The sensing portion 234 may include a dye-impregnated polymer that includes and/or releases fluorescent dyes, which are excitable at selected wavelengths of light. For instance, the dye 264 may include one or more of a platinum (II) based dye, a palladium(II) based dye, a ruthenium(II) based dye, or a hemoglobin based dye. For example, the dye 264 may include platinum octaethylporphyrin. Depending upon a partial pressure of oxygen molecules 266 (e.g., an amount of a quencher) within the urine flowing through flow pathway 130 of the oxygen-sensing assembly 104, a fluorescence (e.g., an amplitude and/or duration of a fluorescence) of the dye 264 may vary. Furthermore, as described above, based on the fluorescence response (e.g., an amplitude and/or duration of the fluorescence response) of the dye 264, the control system 106 may determine oxygen levels within the urine.

In some embodiments, the sensing portion 234 may be disposed directly on the distal end of the optical fiber 232. In alternative embodiments, the sensing portion 234 may be separate and distinct from the optical fiber 232 (e.g., disposed away from the distal end of the optical fiber 232). Additionally, the sensing portion 234 may be sized, shaped, and configured to be disposed within the fluid flowing through the flow pathway 130 of the oxygen-sensing assembly 104. Furthermore, the oxygen sensor 220 may operate via any of the manners described above in regard to FIG. 1.

FIG. 3 shows a method 300 that the control system 106 may utilize to determine a risk of acute kidney injury (e.g., urinary hypoxia) in a patient. Referring to FIGS. 1-3 together, in some embodiments, the method 300 may include generating an excitation light, as shown in act 302 of FIG. 3. For example, the optical module 136 of the control system 106 may generate the excitation light. In some embodiments, the optical module 136 of the control system 106 may generate the excitation light to have a selected wavelength of about 432 nm.

Additionally, the method 300 may include causing the excitation light to be transmitted to a sensing portion 134 of an oxygen sensor 120, as shown in act 304 of FIG. 3. For example, the optical module 136 may transmit the excitation light to the sensing portion 134 of the oxygen sensor 120 through an optical fiber 132 of the oxygen sensor 120. As discussed above, the sensing portion 134 of the oxygen sensor 120 may be disposed within a fluid flowing through a flow pathway 130 of an oxygen-sensing assembly 104 of a catheter assembly 100.

In some embodiments, the method 300 may optionally include causing the excitation light to be transmitted to an additional sensing portion 144 of an additional oxygen sensor 140, as show in act 306 of FIG. 3. As discussed above, the additional sensing portion 144 of the additional oxygen sensor 140 may be disposed within a lumen 112 of a urinary catheter 102 of the catheter assembly 100. The optical module 136 of the control system 106 may transmit the excitation light to the additional sensing portion 144 of the additional oxygen sensor 140 via any of the manners described above.

The method 300 may further include receiving return light from the sensing portion 134 of the oxygen sensor 120, as shown in act 308 of FIG. 3. For example, as described above, the sensing portion 134 of the oxygen sensor 120 may include a dye-impregnated polymer that releases fluorescent dyes 264, which are excitable at selected wavelengths of light and may have a fluorescence response to the excitation light. In some embodiments, the optical module 136 of the control system 106 may receive the return light from the sensing portion 134 via the optical fiber 132.

Furthermore, the method 300 may optionally include receiving return light from the additional sensing portion 144 of the additional oxygen sensor 140 of the oxygen-sensing assembly 104, as shown in act 310 of FIG. 3. The optical module 136 of the control system 106 may receive the return light from the additional sensing portion 144 of the additional oxygen sensor 140 via any of the manners described above in regard to the sensing portion 134 of the oxygen sensor 120.

The method 300 may optionally include receiving temperature data and flowrate data from the temperature sensor 124 and the flowrate sensor 122, as shown in act 312 of FIG. 3. For example, as discussed above, the temperature sensor 124 and the flowrate sensor 122 may be operably coupled to the control system 106 (e.g., the data acquisition system 146 of the control system 106) and may provide data related to the temperature and flowrate of a fluid (e.g., urine) flowing through the flow pathway 130 of the oxygen-sensing assembly 104.

Also, the method 300 may include comparing the return light received from the sensing portion 134 of the oxygen sensor 120 and/or the additional sensing portion 144 of the additional oxygen sensor 140 to the excitation light provided by the optical module 136, as shown in act 314 of FIG. 3. For example, in some embodiments, the optical module 136 of the control system 106 may provide a sinusoidally modulated excitation light, and the sensing portion 134 of the oxygen sensor 120 and/or additional sensing portion 144 of the additional oxygen sensor 140 may return a phase-shifted, sinusoidally modulated return light. Furthermore, the control system 106 may measure a phase shift of the phase-shifted, sinusoidally modulated return light relative to the sinusoidally modulated excitation light.

The method 300 may also include determining oxygen levels within the fluid flowing through the flow pathway 130 of the oxygen-sensing assembly 104 and/or the fluid flowing through the lumen 112 of the urinary catheter 102 of the catheter assembly 100, as shown in act 316 of FIG. 3. For example, the control system 106 may determine oxygen levels within the fluid based on the measured phase shift of the phase-shifted sinusoidally modulated return light relative to the sinusoidally modulated excitation light based on the Stern-Vollmer-Theory described above in regard to FIG. 1. In some embodiments, determining oxygen levels may include determining dissolved oxygen concentrations (mg/L), head space oxygen gas concentrations (%), dissolved oxygen readings, etc. In some embodiments, the control system 106 may determine oxygen level within the fluid flowing through the flow pathway 130 of the oxygen-sensing assembly 104 and/or the fluid flowing through the lumen 112 of the urinary catheter 102 of the catheter assembly 100 in real-time based on measurements taken with the oxygen sensor 120 and/or the additional oxygen sensor 140. In additional embodiments, the control system 106 may further determine additional markers such as, for example, pH, $CO_2$, bladder pressure, abdominal pressure, etc., utilizing the oxygen sensor 120, the additional oxygen sensor 140, the temperature sensor 124, and/or the flowrate sensor 122.

In some embodiments, determining oxygen levels within the fluid flowing through the flow pathway 130 of the oxygen-sensing assembly 104 and/or the fluid flowing through the lumen 112 of the urinary catheter 102 of the catheter assembly 100 may include adjusting the oxygen levels based on a detected temperature and flowrate of the fluid. For instance, the control system 106 may adjust determined oxygen levels based on the detected temperature of the fluid utilizing Henry's Law combined with Van't Hoff's equation, as described above in regard to FIG. 1. Additionally, the control system 106 may adjust determined oxygen levels based on the detected flowrate of the fluid. For instance, the detected flowrate may indicate how long the fluid has been out of the bladder of the patient. Accordingly, the control system 106 can adjust the determined oxygen levels based on how long the fluid has been out of the bladder and/or kidney of the patient and the fluid temperature, so that the determined oxygen levels reflect oxygen levels of the fluid within the bladder of the patient. For instance, the control system 106 may utilize one or more algorithms having inputs of a volume of a urine column between the renal medulla and the oxygen sensor 120, a diffusion of oxygen across kidney, ureter, bladder, urinary catheter, and/or oxygen-sensing assembly walls and membranes, flow rates of the urine, correlations between kidney PO2 and urine PO2, and body temperature to adjust the determined oxygen levels (e.g., output renal medulla PO2). Additionally, the control system 106 may plot determined oxygen levels (e.g., output renal medulla PO2) over time for a given patient.

Additionally, the method 300 may include determining oxygen tension of the fluid flowing through the flow pathway 130 of the oxygen-sensing assembly 104 and/or the fluid flowing through the lumen 112 of the urinary catheter 102 of the catheter assembly 100, as shown in act 318 of FIG. 3. In some embodiments, the method 300 may include measuring the oxygen tension (pO2) (mmHg) (e.g., partial pressure) directly with the oxygen sensor 120. Additionally, the method 300 may include determining urinary oxygen tension (pO2) (mmHg) and/or mean medullary oxygen tension (mmHg) based on the oxygen levels determined in act 316 of FIG. 3.

The method 300 may further include determining a risk of acute kidney injury (e.g., urinary hypoxia) of a patient based on the oxygen tension(s) determined in act 318 of FIG. 3, as shown in act 320 of FIG. 3. For example, the control system 106 may determine the risk of developing future acute kidney injury in the patient (e.g., kidney hypoxia). Additionally, the control system 106 may cause an indication of the risk of developing future acute kidney injury to be displayed on the user interface 154 of the control system 106. Moreover, the method 300 may include continuously repeating acts 302 through 320 to continuously monitor oxygen tension within the urine of the patient and to continuously monitor for risk of acute kidney injury in the patient. Furthermore, the control system 106 may cause an indication of an instantaneous/real-time urine flow through the catheter assembly 100 to be displayed on the user interface 154 of the control system 106.

In view of the foregoing, the catheter assembly 100 of the present disclosure may provide a continuous and real-time monitor of kidney hypoxia for patients. Furthermore, because the catheter assembly 100 monitors the urine of the patient in real-time, the catheter assembly 100 may remove the inherent lag time present in conventional methods of diagnosing patients at risk of for a subsequent acute kidney injury (e.g., methods of measuring serum creatinine levels). As will be appreciated by one of ordinary skill in the art, by detecting kidney hypoxia as indicated by urinary hypoxia, the catheter assembly 100 may allow for detection of patients at risk for subsequent acute kidney injury. By identifying these patients at risk, before permanent kidney injury occurs, the catheter assembly 100 may prevent AKI, and thus reduce hospital stay durations, medical costs, improve recovery times, and may ultimately save lives.

Additionally, the catheter assembly 100 of the present disclosure may provide a relatively non-invasive method for continuously monitoring for kidney hypoxia and risk for acute kidney injury in patients. For instance, perioperative patients typically have a urinary catheter placed before surgery, and use of the catheter assembly 100 of the present disclosure with urinary catheter 102 placed pre-operatively does not increase the invasiveness of the already placed catheter. Critically ill non-operative patients also frequently have urinary catheters and are at significant risk for acute kidney injury. One advantage of the catheter assembly 100 of the present disclosure is that the catheter assembly 100 may be introduced into any urinary catheter, even urinary catheters that are already in place in the patient. As discussed above, all of the measurements (e.g., oxygen, temperature, and flowrate measurements) take place within the catheter assembly 100. For instance, the oxygen-sensing assembly 104 may be placed after the urinary catheter 102 is placed without requiring any more invasive procedures. Furthermore, the oxygen-sensing assembly 104 may give healthcare providers more flexibility, as any decision regarding whether or not to include the oxygen-sensing assembly 104 need not be made prior to surgery or hospital admission but can be made anytime throughout a patient's care without requiring additional invasive procedures. Accordingly, the catheter assembly 100 of the present disclosure may reduce the risk of infection and disease by not increasing invasive procedures. Additionally, the catheter assembly 100 may be able usable with a wide variety of different urinary catheters, and accordingly, may provide a more versatile catheter assembly to health care providers. Moreover, in comparison to conventional catheter assemblies, the catheter assembly 100 of the present disclosure provides for simpler installation and less risk of infection, fiber breakage, and leaching of fluorescent dyes into the body of the patient. Also, the catheter assembly 100 is connected to the control system 106 via reusable cables, making the oxygen-sensing assembly disposable and less expensive than conventional fiber-up-catheter systems. Furthermore, the catheter assembly 100 may provide real-time urinary flowrates that may allow assessment of clinical interventions, such as vasoactive medications and administration of fluids.

Figure 4:
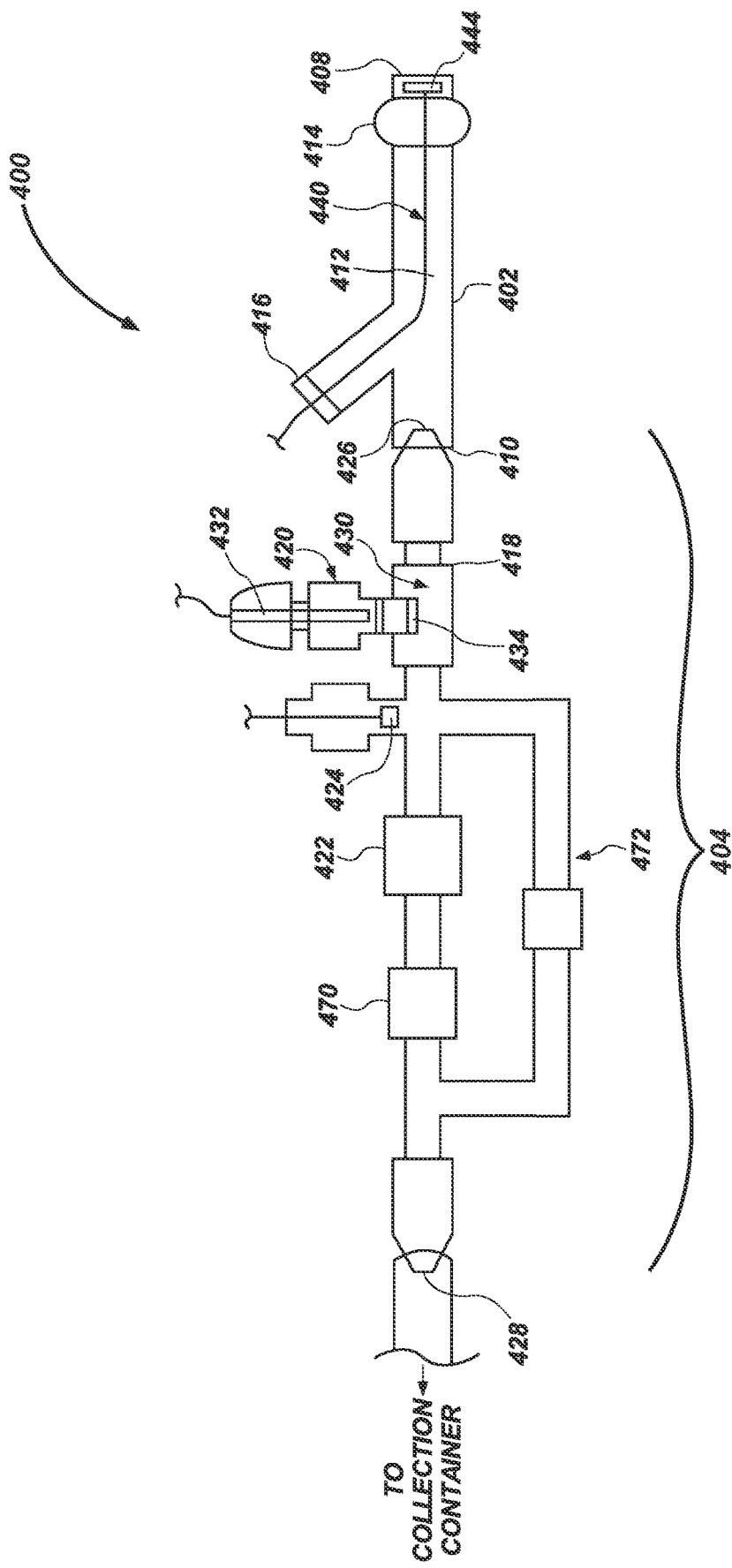
FIG. 4 is a schematic representation of a catheter assembly having an oxygen-sensing assembly having a check valve configuration according to additional embodiments of the present disclosure.

FIG. 4 shows a catheter assembly 400 according to one or more embodiments of the present disclosure. As shown in FIG. 4, similar to the catheter assembly 100 of FIG. 1, the catheter assembly 400 may include a urinary catheter 402 and an oxygen-sensing assembly 404 in fluid communication with the urinary catheter 402. Additionally, the catheter assembly 400 may be operably coupled to a control system 106 as shown and described above in regard to FIGS. 1-3. Additionally, the oxygen-sensing assembly 404 may include a housing 418, an oxygen sensor 420, a flowrate sensor 422, and a temperature sensor 424. The oxygen sensor 420, the flowrate sensor 422, and the temperature sensor 424 may include any of the oxygen sensors, flowrate sensors, and temperature sensors described above in regard to FIG. 1. The housing 418 may include an inlet end 426 and an outlet end 428 and may define a flow pathway 430 between the inlet end 426 and the outlet end 428. The inlet end 426 of the housing 418 may be attachable to the outlet end 410 of the urinary catheter 402 via any connection methods known in the art. The oxygen sensor 420, the temperature sensor 424, and the flowrate sensor 422, may be disposed along the flow pathway 430 in series.

The catheter assembly 400 may further include a check valve 470 downstream of the oxygen sensor 420, the temperature sensor 424, and the flowrate sensor 422 along the flow pathway 430 of the oxygen-sensing assembly 404. Furthermore, in some embodiments, the catheter assembly 400 may include a relief valve and pathway 472 that has a higher cracking pressure (i.e., opening pressure) than the check valve such that flow of the fluid is biased through the check valve. In some embodiments, the relief valve and pathway 472 may extend from a location along the flow pathway 430 of the oxygen-sensing assembly 404 proximate to the temperature sensor 424 and may bypass the flowrate sensor 422. As a result, the temperature sensor 424 and the oxygen sensor 420 cannot be bypassed via the relief valve and pathway 472. Additionally, the relief valve and pathway 472 provides a pathway for fluid flow in the event the flow pathway 430 of the oxygen-sensing assembly 404 becomes clogged or fails (e.g., a check valve within the flow pathway 430 of the oxygen-sensing assembly 404 becomes clogged or fails).

Figure 5:
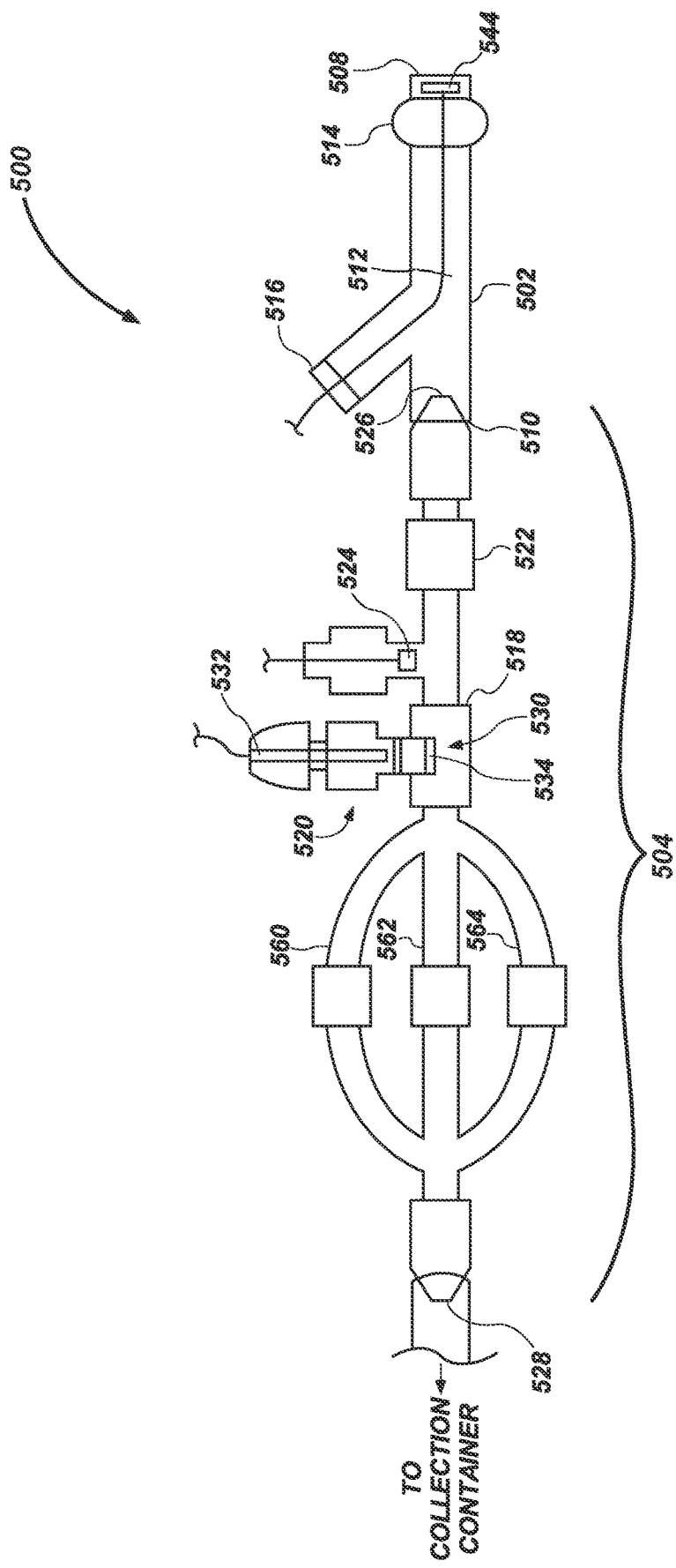
FIG. 5 is a schematic representation of a catheter assembly having an oxygen-sensing assembly having an additional check valve configuration according to additional embodiments of the present disclosure.

FIG. 5 shows a catheter assembly 500 according to one or more embodiments of the present disclosure. As shown in FIG. 5, similar to the catheter assembly 100 of FIG. 1, the catheter assembly 500 may include a urinary catheter 502 and an oxygen-sensing assembly 504 in fluid communication with the urinary catheter 502. Additionally, the catheter assembly 500 may be operably coupled to a control system 106 as shown and described above in regard to FIGS. 1-3. Additionally, the oxygen-sensing assembly 504 may include a housing 518, an oxygen sensor 520, a flowrate sensor 522, and a temperature sensor 524. The oxygen sensor 520, the flowrate sensor 522, and the temperature sensor 524 may include any of the oxygen sensors, flowrate sensors, and temperature sensors described above in regard to FIG. 1. The housing 518 may include an inlet end 526 and an outlet end 528 and may define a flow pathway 530 between the inlet end 526 and the outlet end 528. The inlet end 526 of the housing 518 may be attachable to the outlet end 510 of the urinary catheter 502 via any connection methods known in the art. The flowrate sensor 522, the temperature sensor 524, and the oxygen sensor 520 may be disposed along the flow pathway 530 in series.

The catheter assembly 500 may include three fluid pathways 560, 562, 564 in parallel, each have a check valve, and each having a same cracking pressure (i.e., opening pressure). In additional embodiments, one or more the check valves of the three fluid pathways 560, 562, 564 may have a higher cracking pressure. In some embodiments, the three fluid pathways 560, 562, 564 may be disposed after the flowrate sensor 522, the temperature sensor 524, and the oxygen sensor 520 along the flow pathway 530 of the oxygen-sensing assembly 504. Additionally, the three fluid pathways 560, 562, 564 provide pathways for fluid flow in the event the flow pathway 530 of the oxygen-sensing assembly 504 becomes clogged or fails (e.g., a check valve within the flow pathway 530 of the oxygen-sensing assembly 504 becomes clogged or fails). Moreover, the three fluid pathways 560, 562, 564 provide multiple safeguards in the event one of the three fluid pathways 560, 562, 564 also fails.

Additional non limiting example embodiments of the disclosure are described below.

Embodiment 1: A catheter assembly, comprising: a urinary catheter comprising at least one lumen extending between an inlet end and an outlet end; an oxygen-sensing assembly in fluid communication with the urinary catheter, the oxygen-sensing assembly comprising: a housing having flow pathway extending between an inlet end and an outlet end thereof, wherein the inlet end of the housing is attachable to the outlet end of the urinary catheter; an oxygen sensor in operable communication with the flow pathway of the housing, the oxygen sensor configured to detect oxygen levels of a fluid flowing through the flow pathway; a flowrate sensor disposed between the oxygen sensor and the inlet end of the housing and configured to detect a flowrate of the fluid flowing through the flow pathway; and a temperature sensor disposed downstream of the oxygen sensor and configured to detect a temperature of the fluid flowing through the flow pathway; and a control system operably coupled to the oxygen sensor, the flowrate sensor, and the temperature sensor, the control system comprising: at least one processor; and at least one non-transitory computer-readable storage medium storing instructions thereon that, when executed by the at least one processor, cause the control system to: receive a detected oxygen levels, a detected flowrate, and a detected temperature of the fluid flowing through the flow pathway; and based at least partially on one or more of the detected oxygen levels and the detected temperature, determine a measurement of an oxygen tension of the fluid flowing through the flow pathway of the housing.

Embodiment 2: The catheter assembly of embodiment 1, wherein the oxygen sensor comprises a fiber-optic sensor.

Embodiment 3: The oxygen-sensing assembly of embodiment 1, wherein the oxygen sensor comprises a Fiber Bragg grating sensor.

Embodiment 4: The oxygen-sensing assembly of embodiment 1, wherein the oxygen sensor comprises an electrochemical sensor.

Embodiment 5: The catheter assembly of embodiment 1, wherein the oxygen sensor comprises: an optical fiber extending at least partially into the housing of the oxygen-sensing assembly; and a sensing portion disposed at least partially within the flow pathway of the housing and exposed to the fluid flowing through the flow pathway of the housing, wherein the optical fiber is configured to transmit light through a distal end of the optical fiber and toward the sensing portion and to receive light from the sensing portion through the distal end of the optical fiber.

Embodiment 6: The catheter assembly of embodiment 5, wherein the control system further comprises instructions that, when executed by the at least one processor, cause the control system to: receive light through the optical fiber originating from the sensing portion of the fiber-optic sensor; analyze the light to determine a correlating fluorescence; and based on the determined fluorescence, determine the measurement of an oxygen tension of the fluid flowing through the flow pathway of the housing.

Embodiment 7: The catheter assembly of embodiments 2-6, wherein the oxygen sensor further comprises a barrier disposed between the optical fiber and the sensing portion and configured to prevent the optical fiber from coming into contact with the fluid flowing through the flow pathway of the housing.

Embodiment 8: The catheter assembly of embodiments 3-7, wherein the sensing portion comprises a dye-impregnated polymer that is excitable at a selected wavelength.

Embodiment 9: The catheter assembly of embodiments 1-8, wherein the oxygen-sensing assembly further comprises an additional oxygen sensor disposed within the at least one lumen of the urinary catheter and at a tip of the at least one lumen.

Embodiment 10: The catheter assembly of embodiment 9, wherein the additional oxygen sensor comprises: an additional optical fiber extending into the at least one lumen of the catheter; and an additional sensing portion disposed on a distal end of the optical fiber within the lumen of the catheter, wherein the additional optical fiber is configured to transmit light through a distal end of the additional optical fiber and toward the additional sensing portion and to receive light from the additional sensing portion through the distal end of the additional optical fiber.

Embodiment 11: An oxygen-sensing assembly for attachment to a urinary catheter, the oxygen-sensing assembly comprising: a housing having a flow pathway extending between an inlet end and an outlet end thereof; and an oxygen sensor in operable communication with the flow pathway of the housing, the oxygen sensor configured to detect oxygen levels of a fluid flowing through the flow pathway.

Embodiment 12: The oxygen-sensing assembly of embodiment 11, wherein the oxygen sensor comprises a fiber-optic sensor.

Embodiment 13: The oxygen-sensing assembly of embodiments 11 and 12, wherein the oxygen sensor comprises a Fiber Bragg grating sensor.

Embodiment 14: The oxygen-sensing assembly of embodiment 11, further comprising: a flowrate sensor disposed between the oxygen sensor and the inlet end of the housing and configured to detect a flowrate of the fluid flowing through the flow pathway; and a temperature sensor disposed downstream of the oxygen sensor and configured to detect a temperature of the fluid flowing through the flow pathway.

Embodiment 15: The oxygen-sensing assembly of embodiment 11, wherein the oxygen sensor comprises: an optical fiber extending at least partially into the housing of the oxygen-sensing assembly; and a sensing portion disposed at least partially within the flow pathway of the housing and exposed to the fluid flowing through the flow pathway of the housing, wherein the optical fiber is configured to transmit light through a distal end of the optical fiber and at the sensing portion and to receive light from the sensing portion through the distal end of the optical fiber.

Embodiment 16: The catheter assembly of embodiment 15, wherein the sensing portion comprises a dye-impregnated polymer that is excitable at a selected wavelength.

Embodiment 17: The oxygen-sensing assembly of embodiments 11-16, further comprising a one-way valve disposed within the housing downstream from the oxygen sensor along the flow pathway.

Embodiment 18: The catheter assembly of embodiments 11-17, wherein the oxygen-sensing assembly further comprises additional oxygen sensor disposable within a lumen of the urinary catheter.

Embodiment 19: The oxygen-sensing assembly of embodiment 11, further comprising at least one relief valve oriented parallel to at least a portion of the flow pathway.

Embodiment 20: A method, comprising: attaching an oxygen-sensing assembly to a urinary catheter; disposing the urinary catheter within a bladder of a subject; detecting oxygen levels of a fluid flowing through the urinary catheter and through a flow pathway of a housing of the oxygen-sensing assembly with an oxygen sensor; detecting a flowrate of the fluid flowing through the flow pathway with a flowrate sensor; detecting a temperature of the fluid flowing through the flow pathway with a temperature sensor; and based at least partially on one or more of the detected oxygen levels and the detected temperature of the fluid, determining a measurement of an oxygen tension of the fluid flowing through the flow pathway.

Embodiment 21: The method of embodiment 20, further comprising positioning an additional oxygen sensor within a lumen of the urinary catheter.

Embodiment 22: The method of embodiments 20 and 21, wherein detecting a level of oxygen tension of a fluid further comprises: transmitting light at a selected wavelength through an optical fiber of the oxygen sensor and toward a sensing portion of the oxygen sensor disposed within the flow pathway; receiving light through the optical fiber of the oxygen sensor emitted from the sensing portion of the oxygen sensor; analyzing the received light to determine a correlating fluorescence; and determining a urinary oxygen tension based on the determine fluorescence.

Embodiment 23: The method of embodiments 20-22, further comprising determining from the determined measurement of the oxygen tension of the fluid flowing through the flow pathway if urinary hypoxia is indicated.

Embodiment 24: The method of embodiment 20, further comprising calculating via one or more algorithms a medullary pO2.

Embodiment 25: The method of embodiment 20, further comprising displaying a real-time urine flowrate on a user interface of a control system.

While the present invention has been described herein with respect to certain illustrated embodiments, those of ordinary skill in the art will recognize and appreciate that it is not so limited. Rather, many additions, deletions, and modifications to the illustrated embodiments may be made without departing from the scope of the invention as claimed, including legal equivalents thereof. In addition, features from one embodiment may be combined with features of another embodiment while still being encompassed within the scope of the invention as contemplated by the inventors. Further, embodiments of the disclosure have utility with different and various tool types and configurations.

What is claimed is:

1. A catheter assembly, comprising:
a urinary catheter comprising at least one lumen extending between an inlet end and an outlet end external to a patient;
an oxygen-sensing assembly in fluid communication with the urinary catheter, the oxygen-sensing assembly comprising:
a housing having a flow pathway extending between an inlet end and an outlet end thereof, wherein the inlet end of the housing is attachable to the outlet end of the urinary catheter;
an oxygen sensor configured to detect at least one oxygen level of a fluid flowing through the flow pathway;
a flowrate sensor configured to detect a flowrate of the fluid flowing through the flow pathway; and
a temperature sensor configured to detect a temperature of the fluid flowing through the flow pathway; and
a control system operably coupled to the oxygen sensor, the flowrate sensor, and the temperature sensor, the control system comprising:
at least one processor; and
at least one non-transitory computer-readable storage medium storing instructions thereon that, when executed by the at least one processor, cause the control system to:
receive the at least one detected oxygen level, the detected flowrate, and the detected temperature of the fluid flowing through the flow pathway; and
based at least partially on at least one of the detected flowrate and the detected temperature, qualify the at least one detected oxygen level to determine a relevance of the at least one detected oxygen level to one or more of a bladder oxygen tension, a kidney oxygen tension, and an oxygen level of the fluid from the patient.

2. The catheter assembly of claim 1, wherein the oxygen sensor comprises a fiber-optic sensor.

3. The oxygen-sensing assembly of claim 1, wherein the oxygen sensor comprises a Fiber Bragg grating sensor.

4. The oxygen-sensing assembly of claim 1, wherein the oxygen sensor comprises an electrochemical sensor.

5. The catheter assembly of claim 2, wherein the oxygen sensor comprises:
an optical fiber extending at least partially into the housing of the oxygen-sensing assembly; and
a sensing portion disposed at least partially within the flow pathway of the housing and exposed to the fluid flowing through the flow pathway,
wherein the optical fiber is configured to transmit light through a distal end of the optical fiber and toward the sensing portion and to receive light from the sensing portion through the distal end of the optical fiber.

6. The catheter assembly of claim 5, wherein the control system further comprises instructions that, when executed by the at least one processor, cause the control system to:
analyze light received by the optical fiber to determine a correlating fluorescence; and
based on the determined correlating fluorescence, determine a measurement of an oxygen tension of the fluid flowing through the flow pathway.

7. The catheter assembly of claim 5, wherein the oxygen sensor further comprises a barrier disposed between the optical fiber and the sensing portion and configured to prevent the optical fiber from coming into contact with the fluid flowing through the flow pathway.

8. The catheter assembly of claim 5, wherein the sensing portion comprises a dye-impregnated polymer that is excitable at a selected wavelength.

9. The catheter assembly of claim 1, wherein the oxygen-sensing assembly further comprises an additional oxygen sensor disposed within the at least one lumen of the urinary catheter and at a tip of the at least one lumen.

10. The catheter assembly of claim 9, wherein the additional oxygen sensor comprises:
an additional optical fiber extending into the at least one lumen of the urinary catheter; and
an additional sensing portion disposed on a distal end of the additional optical fiber within the at least one lumen of the urinary catheter,
wherein the additional optical fiber is configured to transmit light through a distal end of the additional optical fiber and toward the additional sensing portion and to receive light from the additional sensing portion through the distal end of the additional optical fiber.

11. The catheter assembly of claim 1, further comprising at least one of a heating element and a cooling element for heating and cooling the fluid.

12. The catheter assembly of claim 1, wherein the temperature sensor is upstream of the oxygen sensor.

13. The catheter assembly of claim 1, wherein the oxygen sensor comprises:
an excitation portion configured to generate light; and
a sensing portion configured to receive the light from the excitation portion.

14. The catheter assembly of claim 1, wherein the control system further comprises instructions that, when executed by the at least one processor, cause the control system to, based at least partially on the at least one detected oxygen level, determine a risk of acute kidney injury.

15. The catheter assembly of claim 1, wherein the control system further comprises instructions that, when executed by the at least one processor, cause the control system to, based at least partially on the at least one detected oxygen level, the detected flowrate, and the detected temperature, determine an oxygen level of the fluid in the bladder or the kidney of the patient.

16. The catheter assembly of claim 1, wherein the control system further comprises instructions that, when executed by the at least one processor, cause the control system to qualify the at least one detected oxygen level based on an amount of time the fluid has been out of one or both of the bladder of the patient or the kidney of the patient.

17. The catheter assembly of claim 1, wherein the control system further comprises instructions that, when executed by the at least one processor, cause the control system to qualify the at least one detected oxygen level to determine a relevance of the at least one detected oxygen level to an oxygen level of the fluid in the bladder of the patient or the kidney of the patient.

18. The catheter assembly of claim 1, wherein the control system further comprises instructions that, when executed by the at least one processor, cause the control system to qualify the at least one detected oxygen level to determine a relevance of the at least one detected oxygen level to an oxygen level of the fluid between a renal medulla of the patient and the oxygen sensor.

19. A method of using the catheter assembly of claim 1, the method comprising:
disposing the urinary catheter within the bladder of the patient;

detecting, with the oxygen sensor, the at least one oxygen level of the fluid flowing through the urinary catheter and through the flow pathway of the housing of the oxygen-sensing assembly;

detecting the flowrate of the fluid flowing through the pathway with the flowrate sensor; and detecting the temperature of the fluid flowing through the pathway with the temperature sensor.

20. The method of claim 19, further comprising positioning an additional oxygen sensor within the at least one lumen of the urinary catheter.

21. The method of claim 19, wherein detecting, with the oxygen sensor, the at least one oxygen level of the fluid further comprises:

transmitting light at a selected wavelength through an optical fiber of the oxygen sensor and toward a sensing portion of the oxygen sensor disposed within the flow pathway;

receiving light through the optical fiber of the oxygen sensor emitted from the sensing portion of the oxygen sensor;

analyzing the received light to determine a correlating fluorescence; and determining urinary oxygen tension based on the determined correlating fluorescence.

22. The method of claim 19, further comprising determining from the at least one determined oxygen level if urinary hypoxia is indicated.

23. The method of claim 19, further comprising calculating via one or more algorithms a medullary pO2.

24. The method of claim 19, further comprising displaying a real-time urine flowrate on a user interface of the control system.

25. A catheter assembly, comprising:

a urinary catheter comprising at least one lumen extending between an inlet end and an outlet end;

an oxygen-sensing assembly in fluid communication with the urinary catheter, the oxygen-sensing assembly comprising:

a housing having a flow pathway extending between an inlet end and an outlet end thereof, wherein the inlet end of the housing is attachable to the outlet end of the urinary catheter;

an oxygen sensor comprising a fiber-optic sensor configured to detect an oxygen level of a fluid flowing through the flow pathway, the fiber-optic sensor comprising:

an optical fiber extending at least partially into the housing of the oxygen-sensing assembly; and a sensing portion disposed at least partially within the flow pathway of the housing, wherein the optical fiber is configured to transmit light through a distal end of the optical fiber and toward the sensing portion and to receive light from the sensing portion through the distal end of the optical fiber;

a flowrate sensor configured to detect a flowrate of the fluid flowing through the flow pathway; and a temperature sensor configured to detect a temperature of the fluid flowing through the flow pathway; and a control system operably coupled to the oxygen sensor, the flowrate sensor, and the temperature sensor, the control system comprising:

at least one processor; and at least one non-transitory computer-readable storage medium storing instructions thereon that, when executed by the at least one processor, cause the control system to:

receive the detected oxygen level, the detected flowrate, and the detected temperature of the fluid flowing through the flow pathway; and based at least partially on one or more of the detected oxygen level, the detected flowrate, and the detected temperature, determine an oxygen level in a bladder or kidney of a patient.

26. A catheter assembly, comprising:

a urinary catheter comprising at least one lumen extending between an inlet end and an outlet end external to a patient;

an oxygen-sensing assembly in fluid communication with the urinary catheter, the oxygen-sensing assembly comprising:

a housing having a flow pathway extending between an inlet end and an outlet end thereof, wherein the inlet end of the housing is attachable to the outlet end of the urinary catheter;

an oxygen sensor configured to detect at least one oxygen level of a fluid flowing through the flow pathway;

a flowrate sensor configured to detect a flowrate of the fluid flowing through the flow pathway; and a temperature sensor configured to detect a temperature of the fluid flowing through the flow pathway; and a control system operably coupled to the oxygen sensor, the flowrate sensor, and the temperature sensor, the control system comprising:

at least one processor; and at least one non-transitory computer-readable storage medium storing instructions thereon that, when executed by the at least one processor, cause the control system to:

receive the at least one detected oxygen level, the detected flowrate, and the detected temperature of the fluid flowing through the flow pathway; and based at least partially on at least one of the detected flowrate, the detected temperature, and the at least one detected oxygen level, qualify the at least one detected oxygen level to determine a relevance of the at least one detected oxygen level to one or more of a bladder oxygen tension, a kidney oxygen tension, and an oxygen level of the fluid from the patient.

* * * * *

UNITED STATES PATENT AND TRADEMARK OFFICE
CERTIFICATE OF CORRECTION

PATENT NO. : 11,395,616 B2
APPLICATION NO. : 16/121372
DATED : July 26, 2022
INVENTOR(S) : Kai Kuck et al.

It is certified that error appears in the above-identified patent and that said Letters Patent is hereby corrected as shown below:

In the Claims

| | | | |
|---|---|---|---|
| Claim 19, | Column 23, | Line 6, | change "pathway with" to --flow pathway with-- |
| Claim 19, | Column 23, | Line 8, | change "pathway with" to --flow pathway with-- |
| Claim 22, | Column 23, | Line 27, | change "determined" to --detected-- |

Signed and Sealed this
Sixteenth Day of May, 2023

Katherine Kelly Vidal
*Director of the United States Patent and Trademark Office*